United States Patent [19]

Erdei et al.

[11] Patent Number: 4,906,574
[45] Date of Patent: Mar. 6, 1990

[54] FERMENTING DEVICE FOR THE CULTURE OF AEROBIC MICRO-ORGANISMS

[75] Inventors: János Erdei; Ernő Karácsony; László Csermely; Jeno Szilágyi; György Sántha; Péter Seres, all of Debrecen, Hungary

[73] Assignee: Biogal Gyógyszergyár, Debrecen, Hungary

[21] Appl. No.: 205,426

[22] Filed: Jun. 10, 1988

[30] Foreign Application Priority Data

Jun. 12, 1987 [HU] Hungary .............................. 2677/87

[51] Int. Cl.⁴ ............................................. C12N 1/00
[52] U.S. Cl. .................................... 435/243; 435/315; 435/316; 366/303; 366/305; 366/307
[58] Field of Search ................. 435/286, 287, 311–316, 435/243, 253.1, 252; 366/303, 305, 307

[56] References Cited

U.S. PATENT DOCUMENTS

| | | | |
|---|---|---|---|
| 1,985,791 | 12/1934 | McCarroll | 366/305 |
| 2,542,031 | 2/1951 | Humfeld et al. | 435/315 |
| 2,804,379 | 8/1957 | Wistrich et al. | 366/305 |
| 4,519,959 | 5/1985 | Takeuchi et al. | 435/316 |
| 4,655,918 | 4/1987 | Eertink | 435/315 |
| 4,814,278 | 3/1989 | Hamamoto et al. | 435/315 |

FOREIGN PATENT DOCUMENTS

| | | | |
|---|---|---|---|
| 2062310 | 6/1971 | Fed. Rep. of Germany | 435/316 |
| 319238 | 3/1972 | U.S.S.R. | 435/316 |
| 574466 | 9/1977 | U.S.S.R. | 435/315 |

Primary Examiner—James C. Yeung
Attorney, Agent, or Firm—Schweitzer & Cornman

[57] ABSTRACT

A fermenting device for culturing aerobic microorganisms equipped with a plurality of stirrer-agitators also includes a preferably conical baffle screen which is open at the top and the bottom and is spaced from the walls of the fermentor device, and is disposed between each agitator for guiding air dispersed by one agitator into the space under the next agitator for redispersion thereby. Suitably an annular guide member is disposed along the interior walls of the fermentor and under the baffle screen to improve the efficacy of the redispersion. The aerobic fermentation process involves the dispersing of air introduced into the fermentor by a rotated agitator and then conducting the dispersed air by a baffle screen and optional annular guide member to a next agitator for redispersion.

7 Claims, 1 Drawing Sheet

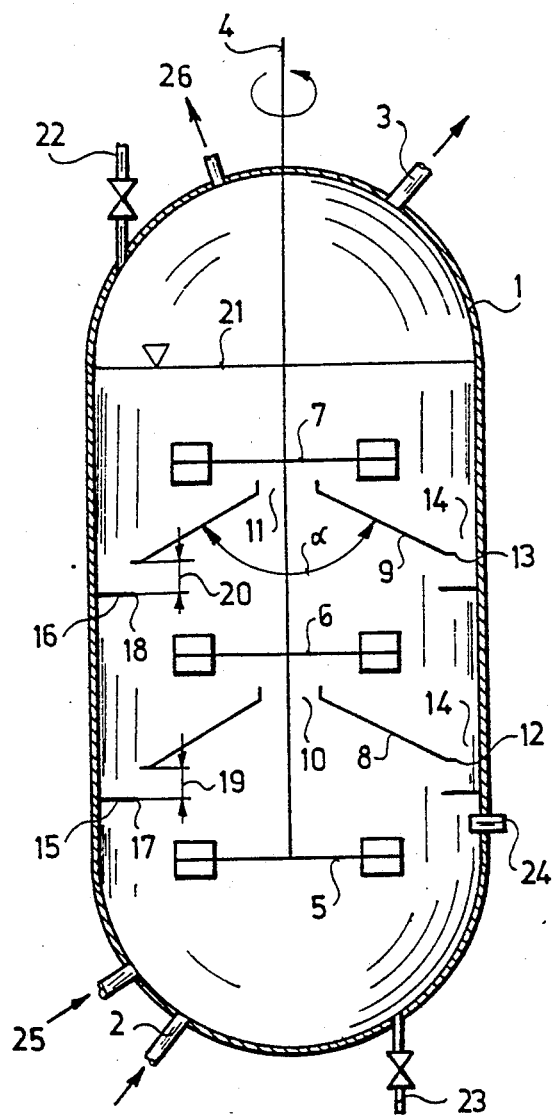

FERMENTING DEVICE FOR THE CULTURE OF AEROBIC MICRO-ORGANISMS

FIELD OF THE INVENTION

The invention relates to a fermenting device for the culturing of aerobic microorganisms.

BACKGROUND OF THE INVENTION

The use of microorganisms in various technologies and manufacturing processes has expanded greatly since the large scale production of antibiotics such as penicillin and since the culturing of aerobic microorganisms has been developed.

Culturing methods based on agitation and aeration were perfected and improved considerably during the past more than 40 years. A large number of publications appeared on this subject (e.g. "Biotechnology", vol. 2. Editor: Brauer, 1985).

In addition to special purpose devices such as devices for tissue cultures, reactors for the purification of effluent, etc. development concentrated mainly on the geometry of the fermentor, the determination of its dimensions and proportions, research and development directed to the shape of the agitators to develop a fermentor which can be universally applied to the production of aerobic culturing of microorganisms, such as in the production of antibiotics, enzymes and amino acids.

These technologies are generally characterized by high oxygen demand. The oxygen required for the metabolism of the microorganisms (dissolved oxygen for the deep-culture method) is mostly provided by agitation and aeration. Agitation and aeration simultaneously perform several important functions:

they assure homogeneity, the distribution of the nutrients in the entire volume of the ferment also in the outgoing metabolites;

provide oxygen supply by causing a considerable fluid gas boundary phase through the dispersion of the blown in air, thus assisting in the dissolution of the oxygen;

making use of the flushing effect of the air assures the removal of the gaseous products of the metabolism.

Most critical of the three functions if the supplying of oxygen. The greater the oxygen consumption of the microorganisms the more air and the more efficient dispersion i.e. agitation are required to assure an oxygen surplus. This however, increases manufacturing cost. Therefore, for a long time each way has been sought to eliminate the need for agitation. Solutions have been found, that at least partly meet this aim, but these have found only limited application. These solutions include the principle of the mammoth pump in which the agitator is surrounded by a large diameter pipe ending above the liquid level and air is blown into the pipe from below, beneath the agitator. A similar solution is the "air lift loop reactor" which employs blown air but in which no agitator is employed. While in these solutions less energy is required to move the fluid and assure relatively oxygen rich conditions within the pipe. The culture (ferment) pouring out on top of the pipe until it reenters the pipe must pass along a relatively long, dead, unaerated a space to which very few cultures can be exposed without damage.

Aeration by a fluid jet appears to be preferable. In such aeration a pump causes the ferment to circulate over an external circle by exhausting the fluid from the bottom of the fermentor and pressing it back to the fermentor (jet-reactor) dome as a jet under several atmospheres pressure. As the liquid jet passes through the space in top of the device it absorbs sufficient gas to endure the full oxygen surplus for the entire fermentor culture. Although the cost of power is very favorable in this use, the additional investment can be recaptured only in new fermentors and above a certain fermentor size.

The effort to reduce the specific power requirements led to a new fermentor called "TOURS" which consists of a horizontally arranged annular pipe in which the liquid moves both in a circle as well as up and down. The relatively large air space and the low hydrostatic pressure provides favorable conditions for the oxygen supply but also this device has its drawbacks; not only can its cost be amortised only in new fermentors, but it also has a considerably large footprint that requires large floor space. (A. Einsele Swiss Biotechn. 46/1986, p. 21-24).

None of the solutions outlined above is suitable to reduce at small extra cost the power demand of conventional fermentors.

DESCRIPTION OF THE INVENTION

The invention is based on the recognition that the oxygen supply can be enhanced by repeated dispersion of the air blast. In the conventional; devices the main reason for the low efficiency of the oxygen input derives from the physical fact that air dispersed by agitators is quickly agglomerating and reduces the liquid/gas boundary phase, which results in the slowdown of the gas exchange. The agitators above the lowermost agitator have little effect on this agglomeration because only a small part of the bubbles get into the active mixing zone. the rest of the bubbles avoid the agitator without any of the essential redispersion or otherwise escape along the interior wall of the device.

The aim of the invention is to provide a device for the aerobic culturing of microorganisms, which has a reduced power demand and increases the oxygen supply and which can be applied to existing devices.

This aim is achieved by a device according to the present invention in which a preferably conical baffle screen is arranged between two adjacent agitators. The baffle screen is open at the bottom and at the top and the outer circumference of its lower rim is smaller than the inner circumference of the cylindrical body of the fermentor vessel.

A guide ring is arranged between each baffle screen and the agitator below it. The outer circumference of the ring contacts the inner wall of the cylindrical body of the fermentor while the inner circumference of the guide ring is identical to or smaller than the outer circumference of the lower rim of the baffle screen above.

Suitably the baffle screen have a truncated cone shape and the cone angle lies suitably between 90° and 120°.

The baffle screen shaped and arranged according to the present invention collects the air dispersed by the lowermost agitator, then agglomerates and passes the bubbles into the active mixing zone of the agitator above it so that they are completely redispersed. This process is repeated as many times as there are agitators in the device. Repeated dispersion makes it possible to ensure the same oxygen supply by a smaller amount of air then in conventional fermentors or assure between oxygen supply with an equal amount of air than could have been achieved in the conventional fermentor.

The efficiency of the baffle screen in collecting the air can be considerably enhanced by placing a guide ring beneath each screen and above the agitator below it. This will prevent air from escaping above the cylindrical wall of the fermentor without preventing the vertical movement of the fluid i.e. the ferment. Complete homogeneity can be established in the sectors separated by baffle screens because the baffle screen and guide ring unequivocally determine the direction of the movement of the air without impeding the vertical movement of the ferment.

The solution according to the present invention offers further advantages. As it is well known, the power required to rotate an agitator in a liquid at a given rate can be reduced by blasting a gas such as air below the agitator because a heterodisperse liquid/gas system provides less fluid resistance to the agitator than a liquid alone. In conventional fermentors air is introduced only to the lowermost agitator. Therefore, only this agitator will rotate easier, the rest of the agitators that revolve in a less well dispersed medium will consume more energy.

In the fermentor of the present invention each agitator rotates in an identical heterodisperse liquid/gas system that consumes the least energy, without the need for a separate supply of air to each agitator. This is made possible by the baffle screens disposed between the agitators and the optional annular guide members or guide rings arranged beneath the screens.

DESCRIPTION OF THE PREFERRED EMBODIMENT

The invention is described through a preferred embodiment shown in the sole figure of the drawing which shows in diagrammatical longitudinal section a device according to the invention.

The fermentor has a double-walled cylindrical body 1 which is closed at both of its ends in the form of a semi-circle. At the bottom of the body an air intake opening 2, and at the top an air outlet opening 3 are arranged. At the top of the body 1, there are disposed at least one feeding stud 22, and at the bottom at least one sampling stud 23, further at the bottom a steam inlet 25 and at the top a steam outlet 26. A measuring point 24 is formed on the mantle of the body 1 under the fluid level 21. The cylindrical body 1 can be cooled by a cooling liquid introduced into the double wall and can be heated by a warm liquid or steam introduced into the double wall, as may be required.

A rotary shaft 4 is arranged in the center of the body 1. In the illustrated embodiment three agitators 5, 6, 7 are attached to the shaft. A baffle screen 8 is disposed between the lowermost agitator 5 and the agitator 6 above it, and a baffle screen 9 is arranged between the agitator 6 and the agitator 7 above it. The baffle screens 8 and 9 are conical, preferably of truncated conical shape. the cone angle is suitably between 90° and 120°. The truncated cone is open at the bottom and at the top so that there remains an annular opening 10 between the shaft 4 sand the baffle screen 8. There remains an annular opening 11 free between the shaft 4 and the baffle screen 9.

A slot 14 having the width "b" remains free between the outer circumference 12 of the lower rim of the baffle screen 8 and the cylindrical fermentor 1, and a slot 34 is thus free between the outer circumference 13 of the lower rim of the baffle screen 9 and the cylindrical fermentor body 1. In this manner the outer circumference 12 of the baffle screen 8 and the outer circumference 13 of the baffle screen 9 are, respectively, smaller than the inner circumference of the cylindrical fermentor body 1. The width "b" of the slot 14 suitably depends on the consistency of the material in the fermentor; if the material is thicker, then a greater value should be chosen for the width "b" of the slot 14. The cone angle of the baffle screens 8 and 9, respectively also depends on the consistency of the material in the fermentor.

Annular guide members such as guide rings 15 and 16 are arranged, respectively, between the baffle screen 8 and the agitator 5 below it and the baffle screen 9 and the agitator 6 below it. The outer circumference of these guide rings 15 and 16 is in contact with the inner wall of the cylindrical fermentor body 1 and are suitably attached to it.

The inner circumferences "e" and "f" of the guide rings 15 and 16 is identical to or smaller than the outer circumferences 12 and 13 of the lower rims of the baffle screens 8 and 9, respectively, above the guide rings 15 and 16.

The width of the guide rings 15 and 16 also suitably depends on the consistency of the material in the fermentor 1. The distance "c" between the guide ring 15 and the baffle screen 8 above it and the distance "d" between the guide ring 16 and the baffle screen 9 above it suitably also depends on the consistency of the material in the fermentor 1.

In the fermentor according to the invention, the air entering the fermentor at the bottom through the intake opening 2 is dispersed due to the effect of the agitator 6 in the liquid with which the apparatus is filled to liquid level 21. The once dispersed liquid which contains the agglomerating bubbles is led by the guide ring 15 and the baffle screen 8 into the active mixing zone of the next agitator 6 so that it will be again completely dispersed.

The air bubbles that tend to re-agglomerate are led by the guide ring 16 and the baffle screen 9 into the active mixing zone of the agitator 7 so that they will be again dispersed.

In a model fermentor with mixing on three levels the oxidation of the contents and the quantity of oxygen consumed during the oxidation in aqueous medium has been compared with baffle screens 8, 9 and the guide rings 15, 16 have been placed in the fermentor, an then mixing the contents without these elements in the fermentor. The aeration ratio was 1:0.4.

| revolutions per minute | with baffle screens and guide rings | without baffle screens and guide rings |
| --- | --- | --- |
| 335 | 16.5 | 18.5 |
| 390 | 14.9 | 16.5 |
| 500 | 13.1 | 14.2 |

The data are shown in the following table.

As seen from the table, with identical fermentor cross section when baffle screens and guide rings were applied in accordance with the present invention a larger amount of oxygen was absorbed in the liquid medium. The results were similar also in the case of other ratios of aeration.

The power demand was also examined. In the given model system a nearly 30% reduction of energy demand was obtained in accordance with the present invention. However, the energy saving depends on the layout of the device such as geometry, the size and number of the baffle screens and guide rings. Under optimum design conditions the energy savings might be even greater.

What is claimed:

1. In a fermenting device for culturing aerobic microorganisms, the device having a fermentor body for containing the microorganism in a liquid and having an internal wall, means for introducing air into said fermentor body, a shaft in said body for rotatably mounting a plurality of agitators spaced from each other for dispersing air within the liquid, the improvement which comprises one or more baffle screens within said fermentor body, each of said baffle screens being disposed between two agitators for guiding air displaced by one agitator to an adjacent agitator for redispersion, said baffle screen being open at its top and bottom and at its larger dimension being spaced from the interior wall of said fermentor body.

2. The fermenting device of claim 1, wherein said baffle screen is shaped as a frustum.

3. The fermenting device of claim 2, further comprising one or more annular guide members disposed at the interior wall of said fermentor body, each guide member being associated with a baffle screen and being disposed adjacent to and spaced from the larger circumference of said frustum.

4. The fermenting device of claim 2, wherein the cone angle of the frustum is between about 90° and about 120°.

5. A method for the aerobic fermentation of microorganisms in a fermentor vessel containing the microorganism in a liquid, which comprises introducing air into the liquid at the bottom of the vessel, dispersing the introduced air with a first rotated agitator, conducting the dispersed air to a second rotated agitator through the central part and the marginal part of a vertically disposed baffle screen within said vessel and being spaced from the interior walls of said vessel and redispersing the conducted air by said second rotated agitator.

6. The method of claim 5, wherein said baffle screen disposed between said first and said second rotated agitators has the shape of a frustum and is open at the top and the bottom thereof.

7. The method of claim 5, wherein said step of conducting further comprises conducting the dispersed air that passes between the interior wall and the bottom edge of said baffle screen through a gap formed between an annular guide member disposed along the interior walls of the container below said baffle screen and said bottom edge.

* * * * *